United States Patent [19]
Rosen et al.

[11] Patent Number: 5,599,295
[45] Date of Patent: Feb. 4, 1997

[54] MEDICAL PROBE APPARATUS WITH ENHANCED RF, RESISTANCE HEATING, AND MICROWAVE ABLATION CAPABILITIES

[75] Inventors: Arye Rosen, Cherry Hill, N.J.; Stuart D. Edwards, Los Altos, Calif.; Ronald G. Lax, Grassvalley, Calif.; Hugh R. Sharkey, Redwood City, Calif.; Ingemar H. Lundquist, Pebble Beach, Calif.; Paul Walinsky, Wyndmoor, Pa.

[73] Assignee: Vidamed, Inc., Menlo Park, Calif.

[21] Appl. No.: 555,519

[22] Filed: Nov. 8, 1995

Related U.S. Application Data

[60] Division of Ser. No. 178,176, Jan. 6, 1994, which is a continuation-in-part of Ser. No. 929,638, Aug. 12, 1992, abandoned, and Ser. No. 12,370, Feb. 2, 1993, Pat. No. 5,370,675, and Ser. No. 62,364, May 13, 1993, Pat. No. 5,435,805, and Ser. No. 61,072, May 14, 1993, Pat. No. 5,385,544, and Ser. No. 61,647, May 13, 1993, Pat. No. 5,421,819.

[51] Int. Cl.⁶ ..................................... A61B 17/39
[52] U.S. Cl. ............................................. 604/22
[58] Field of Search ..................... 604/164, 280, 604/19–22, 53; 601/2; 606/39, 45, 32, 47, 48; 607/96, 113, 115, 116, 138, 156, 101, 102

[56] References Cited

U.S. PATENT DOCUMENTS

| | | |
|---|---|---|
| 32,066 | 1/1886 | Leveen . |
| 1,879,249 | 9/1932 | Hansaker .................... 604/280 |
| 1,950,788 | 3/1934 | Ewerhardt et al. . |
| 1,968,997 | 8/1934 | Drucker . |
| 2,008,526 | 7/1935 | Wappler et al. . |
| 2,022,065 | 11/1935 | Wappler . |
| 2,047,535 | 7/1936 | Wappler . |

(List continued on next page.)

FOREIGN PATENT DOCUMENTS

| | | |
|---|---|---|
| 10858/92 | 8/1992 | Australia . |
| 0370890 | 5/1990 | European Pat. Off. . |
| 0453071 | 10/1991 | European Pat. Off. . |
| 0495443 | 7/1992 | European Pat. Off. . |
| 521264A2 | 3/1993 | European Pat. Off. . |
| 2848484 | 5/1979 | Germany . |
| 2941060 | 4/1980 | Germany ................... 606/48 |

(List continued on next page.)

OTHER PUBLICATIONS

Standard Urology Product Catalog, Circon ACMI: Stanford (1992).
Chang, Raymond J. et al, American Heart Journal, 125: 1276–1283 (May, 1993).
Cosman, Eric R. et al, Stereostatic and Functional Neurosurgery, pp. 2490–2499 (Date Unknown).
Diasonics, Brochure DIA 2000 171 CRF May 1988.

(List continued on next page.)

*Primary Examiner*—Manuel Mendez
*Attorney, Agent, or Firm*—Flehr, Hohbach, Test, Albritton & Herbert

[57] ABSTRACT

A medical probe device comprising a catheter having a stylet guide housing with at least one stylet port in a side thereof and stylet guide means for directing a flexible stylet outward through at least one stylet port and through intervening tissue to targeted tissue. The stylet comprises an electrical central conductor which is enclosed within an insulating or dielectric sleeve surrounded by a conductive layer terminated by an antenna to selectively deliver microwave or radio frequency energy to target tissue. One embodiment includes the electrical conductor being enclosed within a non-conductive sleeve which itself is enclosed within a conductive sleeve in a coaxial cable arrangement to form a microwave transmission line terminated by an antenna. Another embodiment includes a resistive element near the distal end of the stylet which couples the center electrode to an outer conductor to generate joulian heat as electromagnetic energy is applied, such as an RF signal.

6 Claims, 10 Drawing Sheets

U.S. PATENT DOCUMENTS

| | | |
|---|---|---|
| 2,118,631 | 5/1938 | Wappler . |
| 2,710,000 | 6/1955 | Cromer et al. . |
| 3,230,957 | 1/1966 | Seifert . |
| 3,339,542 | 9/1967 | Howell . |
| 3,556,079 | 1/1971 | Omizo et al. ............................... 128/2 |
| 3,595,239 | 7/1971 | Petersen . |
| 3,598,108 | 8/1971 | Jamshidi et al. . |
| 3,682,162 | 8/1972 | Colyer . |
| 3,828,780 | 8/1974 | Morrison, Jr. . |
| 3,835,842 | 9/1974 | Iglesias . |
| 3,840,016 | 10/1974 | Lindemann . |
| 3,850,175 | 11/1974 | Iglesias . |
| 3,858,577 | 1/1975 | Bass et al. . |
| 3,884,237 | 5/1975 | O'Malley et al. . |
| 3,924,628 | 12/1975 | Droegemueller et al. . |
| 3,939,840 | 2/1976 | Storz . |
| 3,942,530 | 3/1976 | Northeved . |
| 3,948,270 | 4/1976 | Hasson . |
| 3,991,770 | 11/1976 | Leveen . |
| 4,011,872 | 3/1977 | Komiya . |
| 4,119,102 | 10/1978 | Leveen . |
| 4,121,592 | 10/1978 | Whalley . |
| 4,136,566 | 1/1979 | Christensen . |
| 4,137,920 | 2/1979 | Bonnet . |
| 4,154,246 | 5/1979 | Leveen . |
| 4,204,549 | 5/1980 | Paglione . |
| 4,224,929 | 9/1980 | Furihata . |
| 4,228,809 | 10/1980 | Paglione ............................... 128/804 |
| 4,237,898 | 12/1980 | Whalley . |
| 4,267,828 | 5/1981 | Matsuo . |
| 4,295,467 | 10/1981 | Mann et al. . |
| 4,307,720 | 12/1981 | Weber, Jr. . |
| 4,311,145 | 1/1982 | Esty et al. . |
| 4,311,154 | 1/1982 | Sterzer et al. . |
| 4,312,364 | 1/1982 | Convert et al. . |
| 4,375,220 | 3/1983 | Matvias . |
| 4,397,314 | 8/1983 | Vaguine . |
| 4,402,311 | 9/1983 | Hattori . |
| 4,405,314 | 9/1983 | Cope . |
| 4,411,266 | 10/1983 | Cosman . |
| 4,448,198 | 5/1984 | Turner . |
| 4,452,236 | 6/1984 | Utsugi . |
| 4,470,407 | 9/1984 | Hussein ............................... 606/2 |
| 4,494,539 | 1/1985 | Zenitani et al. . |
| 4,534,347 | 8/1985 | Taylor ............................... 128/303.1 |
| 4,552,554 | 11/1985 | Gould et al. . |
| 4,562,838 | 1/1986 | Walker . |
| 4,565,200 | 1/1986 | Cosman . |
| 4,568,329 | 2/1986 | Mahurkar . |
| 4,580,551 | 4/1986 | Siegmund et al. . |
| 4,594,074 | 6/1986 | Anderson et al. . |
| 4,601,296 | 7/1986 | Yerushalmi . |
| 4,612,940 | 9/1986 | Kasevich et al. . |
| 4,658,836 | 4/1987 | Turner . |
| 4,660,560 | 4/1987 | Klein . |
| 4,669,475 | 6/1987 | Turner . |
| 4,672,962 | 6/1987 | Hershenson . |
| 4,676,258 | 6/1987 | Inokuchi et al. . |
| 4,681,122 | 7/1987 | Winters et al. . |
| 4,682,596 | 7/1987 | Bales et al. . |
| 4,697,595 | 10/1987 | Breyer et al. . |
| 4,700,716 | 10/1987 | Kasevich et al. . |
| 4,706,681 | 11/1987 | Breyer et al. . |
| 4,709,698 | 12/1987 | Johnston et al. . |
| 4,719,914 | 1/1988 | Johnson . |
| 4,753,223 | 6/1988 | Bremer . |
| 4,765,331 | 8/1988 | Petruzzi et al. . |
| 4,769,005 | 9/1988 | Ginsburg et al. . |
| 4,774,949 | 10/1988 | Fogarty . |
| 4,776,086 | 10/1988 | Kasevich et al. . |
| 4,781,186 | 11/1988 | Simpson et al. . |
| 4,784,638 | 11/1988 | Ghajar et al. . |
| 4,785,829 | 11/1988 | Convert et al. . |
| 4,798,215 | 1/1989 | Turner . |
| 4,800,899 | 1/1989 | Elliott . |
| 4,805,616 | 2/1989 | Pao . |
| 4,813,429 | 3/1989 | Eshel et al. . |
| 4,817,601 | 4/1989 | Roth et al. . |
| 4,818,954 | 4/1989 | Flachenecker et al. . |
| 4,822,333 | 4/1989 | Lavarenne . |
| 4,823,791 | 4/1989 | D'Amelio et al. . |
| 4,823,812 | 4/1989 | Eshel et al. . |
| 4,860,744 | 8/1989 | Johnson et al. . |
| 4,865,047 | 9/1989 | Chou et al. . |
| 4,872,458 | 10/1989 | Kanehira et al. . |
| 4,887,615 | 12/1989 | Taylor . |
| 4,893,623 | 1/1990 | Rosenbluth . |
| 4,896,671 | 1/1990 | Cunningham et al. . |
| 4,898,577 | 2/1990 | Badger . |
| 4,905,667 | 3/1990 | Foerster et al. . |
| 4,906,230 | 3/1990 | Maloney et al. . |
| 4,907,589 | 3/1990 | Cosman . |
| 4,911,148 | 3/1990 | Sosnowski et al. . |
| 4,911,173 | 3/1990 | Terwilliger . |
| 4,919,129 | 4/1990 | Weber, Jr. et al. . |
| 4,920,978 | 5/1990 | Colvin . |
| 4,932,958 | 6/1990 | Reddy et al. . |
| 4,936,281 | 6/1990 | Stasz . |
| 4,940,064 | 7/1990 | Desai . |
| 4,943,290 | 7/1990 | Rexroth ............................... 606/49 |
| 4,946,449 | 8/1990 | Davis, Jr. . |
| 4,949,706 | 8/1990 | Thon . |
| 4,950,267 | 8/1990 | Ishihara et al. ............................... 606/12 |
| 4,955,377 | 9/1990 | Lennox et al. . |
| 4,961,435 | 10/1990 | Kitagawa et al. . |
| 4,966,597 | 10/1990 | Cosman . |
| 4,967,765 | 11/1990 | Turner et al. . |
| 4,982,724 | 1/1991 | Saito et al. . |
| 4,998,932 | 3/1991 | Rosen et al. . |
| 4,998,933 | 3/1991 | Eggers et al. . |
| 5,002,558 | 3/1991 | Klein et al. . |
| 5,003,991 | 4/1991 | Takayama et al. . |
| 5,007,437 | 4/1991 | Sterzer . |
| 5,007,908 | 4/1991 | Rydell . |
| 5,010,886 | 4/1991 | Passafaro et al. . |
| 5,026,959 | 6/1991 | Ito et al. . |
| 5,029,588 | 7/1991 | Yock et al. . |
| 5,030,227 | 7/1991 | Rosenbluth et al. . |
| 5,035,695 | 7/1991 | Weber, Jr. et al. . |
| 5,035,696 | 7/1991 | Rydell . |
| 5,045,056 | 9/1991 | Behl . |
| 5,045,072 | 9/1991 | Castillo . |
| 5,055,109 | 10/1991 | Gould et al. . |
| 5,057,105 | 10/1991 | Malone et al. . |
| 5,057,106 | 10/1991 | Kasevich et al. . |
| 5,057,107 | 10/1991 | Parins . |
| 5,059,851 | 10/1991 | Corl et al. . |
| 5,060,660 | 10/1991 | Gambale et al. . |
| 5,071,418 | 12/1991 | Rosenbaum ............................... 606/45 |
| 5,080,660 | 1/1992 | Buelna . |
| 5,083,565 | 1/1992 | Parins . |
| 5,084,044 | 1/1992 | Quint . |
| 5,100,423 | 3/1992 | Fearnot . |
| 5,108,415 | 4/1992 | Pinchuk et al. . |
| 5,109,859 | 5/1992 | Jenkins . |
| 5,112,137 | 5/1992 | Lennox ............................... 606/42 |
| 5,116,615 | 5/1992 | Gokcen et al. . |
| 5,120,316 | 6/1992 | Morales et al. . |
| 5,135,525 | 8/1992 | Biscoping et al. . |
| 5,150,717 | 9/1992 | Rosen et al. . |
| 5,170,787 | 12/1992 | Lindegren . |
| 5,178,620 | 1/1993 | Eggers et al. . |

| | | |
|---|---|---|
| 5,179,962 | 1/1993 | Dutcher et al. . |
| 5,190,539 | 3/1993 | Fletcher et al. . |
| 5,195,965 | 3/1993 | Shantha . |
| 5,195,968 | 3/1993 | Lundquist et al. . |
| 5,197,963 | 3/1993 | Parins ............ 606/41 |
| 5,201,732 | 4/1993 | Parins et al. . |
| 5,207,672 | 5/1993 | Roth . |
| 5,220,927 | 6/1993 | Astrahan et al. . |
| 5,222,953 | 6/1993 | Dowlatshahi . |
| 5,228,441 | 7/1993 | Lundquist . |
| 5,234,004 | 8/1993 | Hascoet et al. ............ 607/102 |
| 5,235,964 | 8/1993 | Abenaim . |
| 5,249,585 | 10/1993 | Turner et al. ............. 607/99 |
| 5,254,088 | 10/1993 | Lundquist et al. . |
| 5,257,451 | 11/1993 | Edwards et al. . |
| 5,273,535 | 12/1993 | Edwards et al. . |
| 5,275,162 | 1/1994 | Edwards et al. . |
| 5,281,213 | 1/1994 | Milder et al. . |
| 5,281,217 | 1/1994 | Edwards et al. . |
| 5,281,218 | 1/1994 | Imran . |
| 5,287,845 | 2/1994 | Paul et al. . |
| 5,290,286 | 3/1994 | Parins . |
| 5,293,868 | 3/1994 | Nardella . |
| 5,293,869 | 3/1994 | Edwards et al. . |
| 5,299,559 | 4/1994 | Bruce et al. . |
| 5,300,068 | 4/1994 | Rosar et al. . |
| 5,300,069 | 4/1994 | Hunsberger et al. . |
| 5,300,070 | 4/1994 | Gentelia et al. . |
| 5,300,099 | 4/1994 | Rudie . |
| 5,301,687 | 4/1994 | Wong et al. . |
| 5,304,134 | 4/1994 | Kraus et al. . |
| 5,304,214 | 4/1994 | Deford . |
| 5,309,910 | 5/1994 | Edwards et al. . |
| 5,313,943 | 5/1994 | Houser et al. . |
| 5,385,544 | 1/1995 | Edwards et al. ............ 604/22 |

FOREIGN PATENT DOCUMENTS

| | | |
|---|---|---|
| 3218314 | 6/1983 | Germany . |
| 3247793 | 7/1983 | Germany ............... 606/47 |
| 3844131 | 12/1989 | Germany . |
| 3838840 | 5/1990 | Germany . |
| 2121675 | 5/1990 | Japan . |
| 9007303 | 7/1990 | WIPO . |
| WO911213 | 8/1991 | WIPO . |
| 9116859 | 11/1991 | WIPO . |
| 9207622 | 5/1992 | WIPO . |
| WO92/10142 | 6/1992 | WIPO . |
| 9210142 | 6/1992 | WIPO . |
| 9221278 | 12/1992 | WIPO . |
| 9221285 | 12/1992 | WIPO . |
| 9304727 | 4/1993 | WIPO . |
| 9308755 | 5/1993 | WIPO . |
| 9308756 | 5/1993 | WIPO . |
| 9320893 | 10/1993 | WIPO . |
| 9320886 | 10/1993 | WIPO . |
| 9308757 | 10/1993 | WIPO . |
| 9320767 | 10/1993 | WIPO . |
| 9320768 | 10/1993 | WIPO . |
| WO93/25136 | 12/1993 | WIPO . |
| 9403759 | 2/1994 | WIPO . |
| 9406377 | 3/1994 | WIPO . |
| 9404222 | 3/1994 | WIPO . |
| 9405226 | 3/1994 | WIPO . |
| 9407549 | 4/1994 | WIPO . |
| 9407410 | 4/1994 | WIPO . |
| 9407411 | 4/1994 | WIPO . |
| 9407412 | 4/1994 | WIPO . |
| 9407413 | 4/1994 | WIPO . |
| 9407441 | 4/1994 | WIPO . |
| 9407446 | 4/1994 | WIPO . |
| 9510253 | 4/1995 | WIPO . |

OTHER PUBLICATIONS

Perinchery, Narayan, "Neoplasms of the Prostate Gland." pp. 378–409 (Date Unknown).

Urology 5th ed., Storz, Jan. 1992.

Transuretheral µwave Thermotherapy for Prostatism: Early Mayo Foundation Experience: Blute, Mayo Clinic Proceedings: vol. 67 May 1992 pp. 417–421.

New Therapies for Benign Prostatic Hyperplasia, Editorial Bruskewitz, Mayo Clinic Proceedings vol. 67 May 1992 pp. 493–495.

Industry Strategies, Urology: "A Multi Billion Dollar Market . . . " Stephen Scala Nov. 19, 1991 pp. 1–32.

U.I. Dept. of Health and Human Services, MMWR 41: 401–404 vol. 41, No. 23, (Jun. 12, 1992).

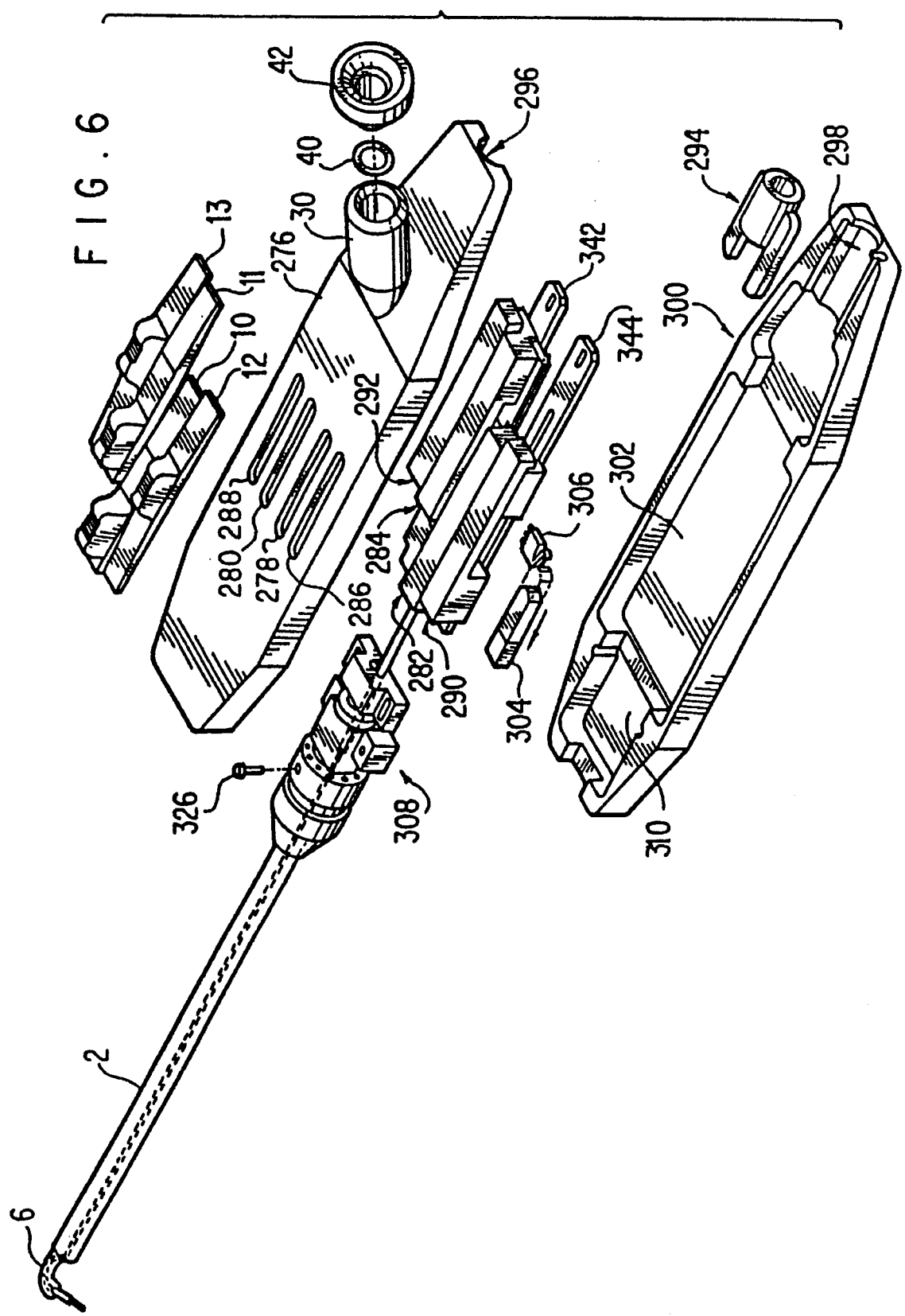

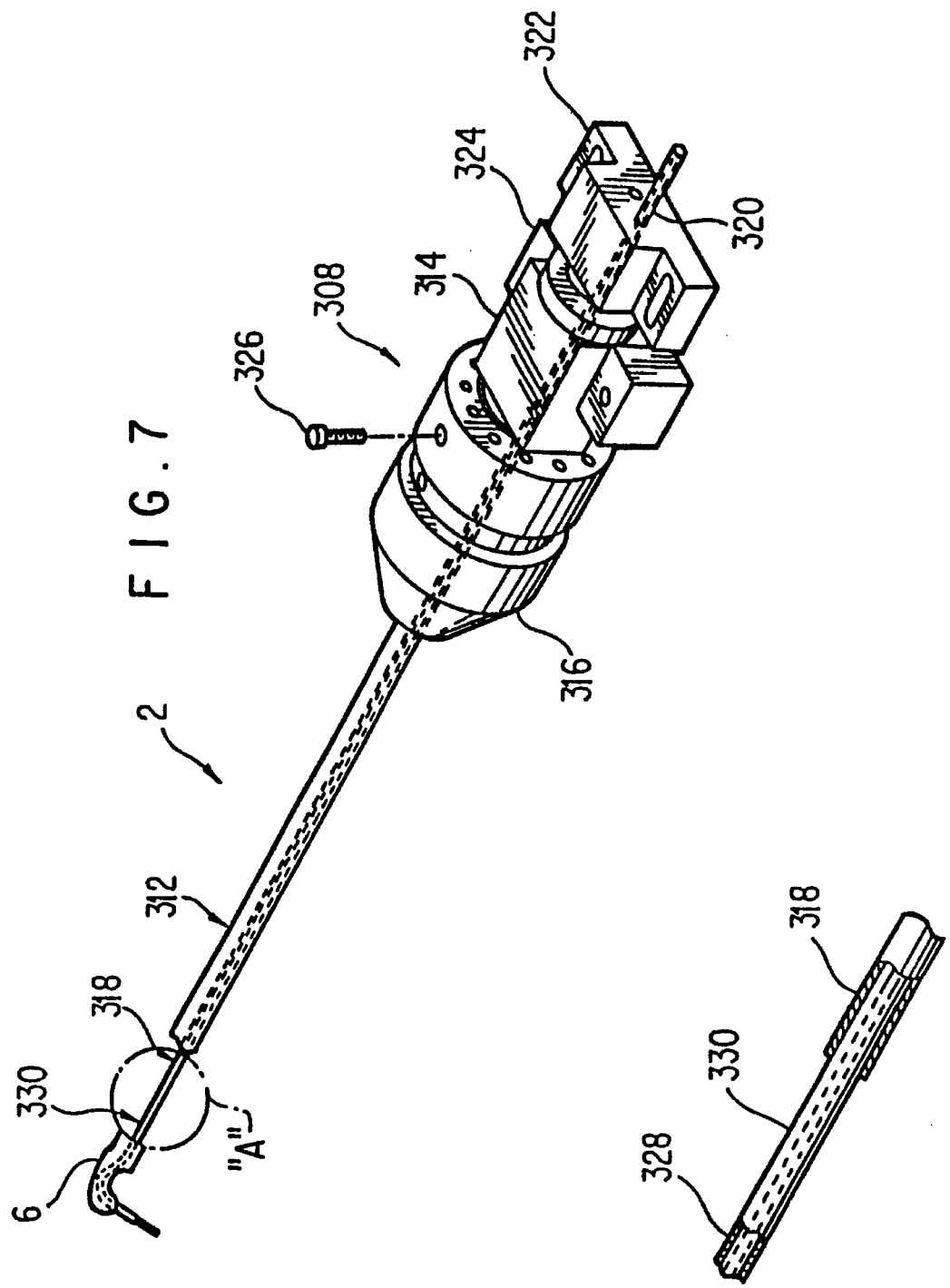

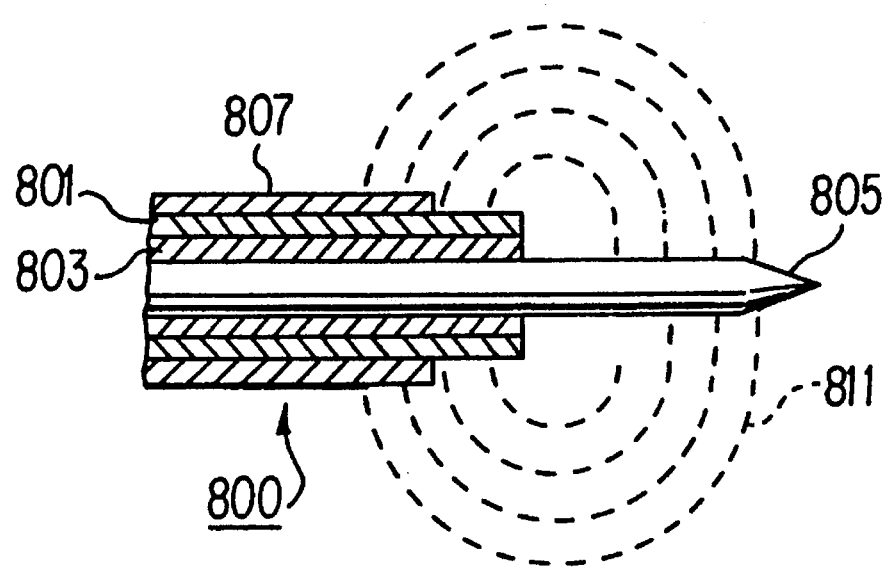
F I G . 11
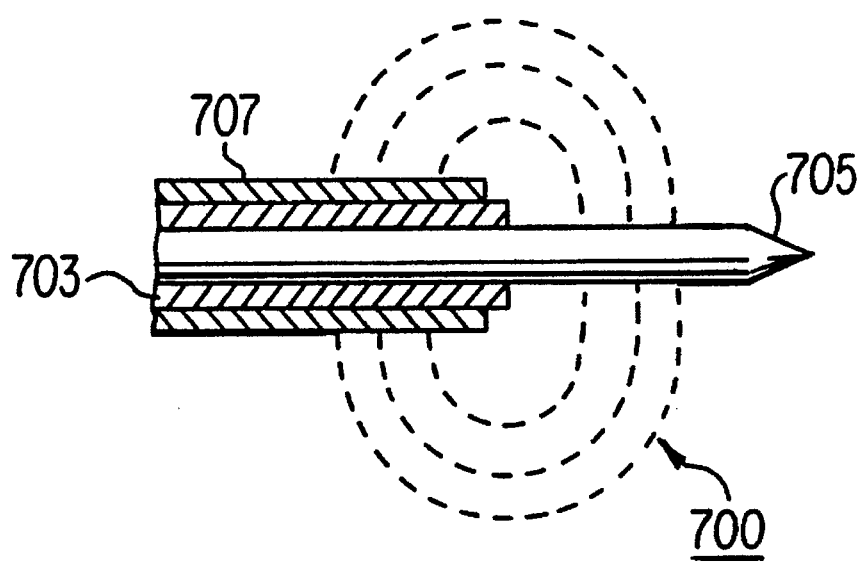
F I G . 12

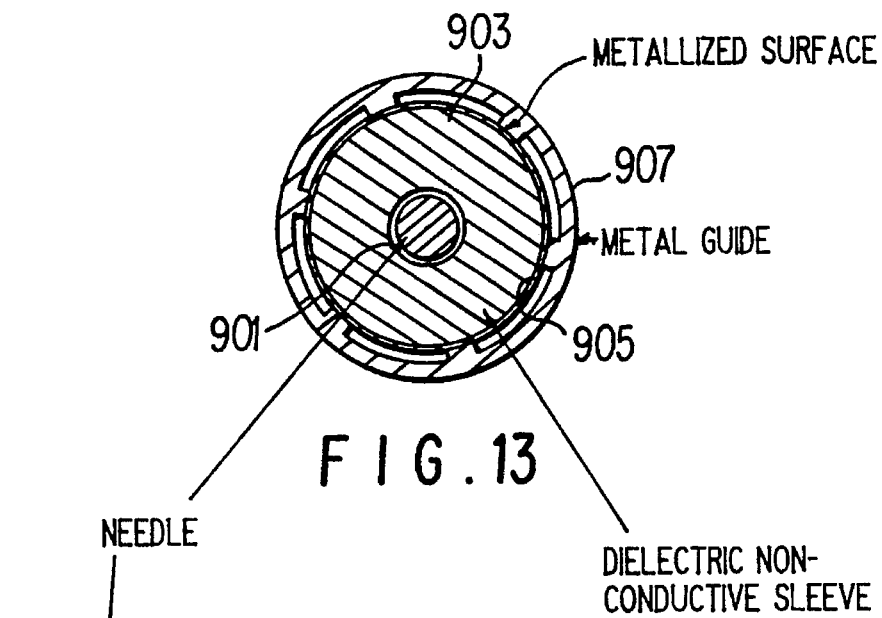
F I G . 13
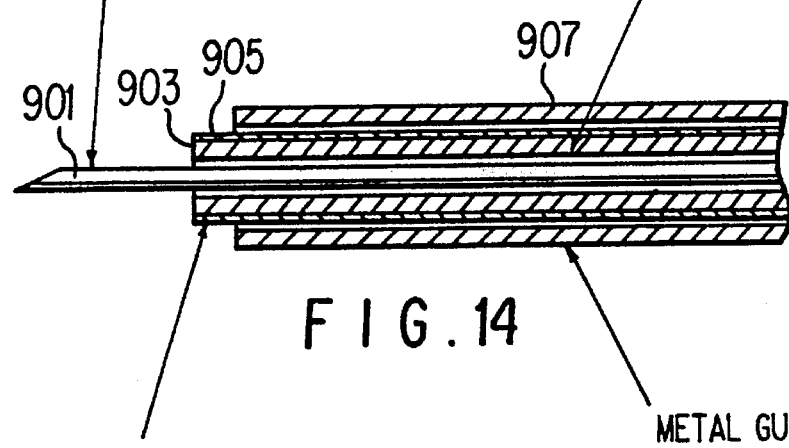
F I G . 14
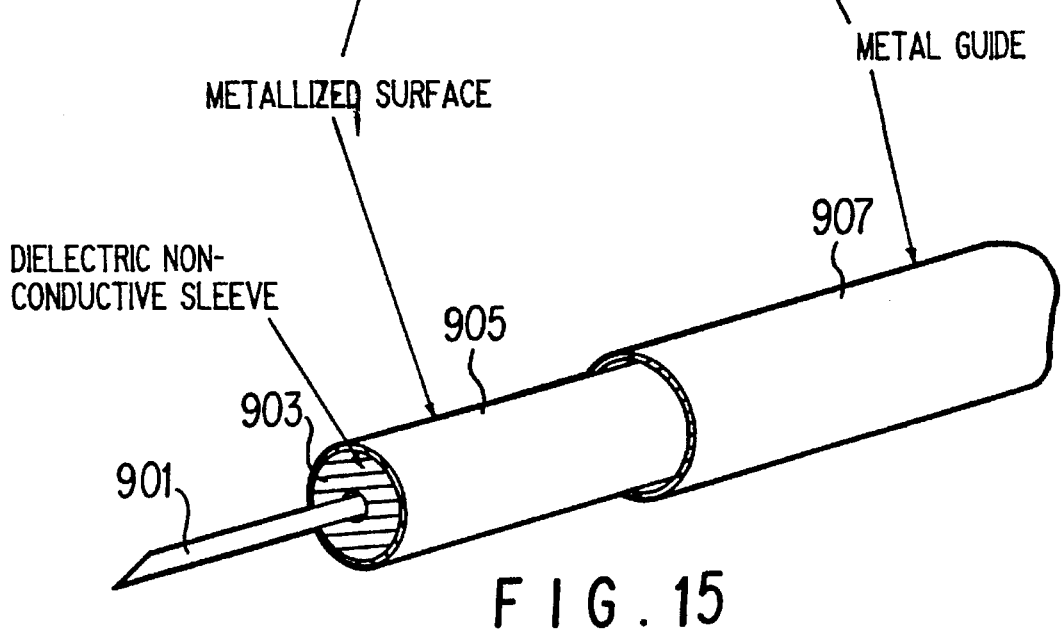
F I G . 15

MEDICAL PROBE APPARATUS WITH ENHANCED RF, RESISTANCE HEATING, AND MICROWAVE ABLATION CAPABILITIES

This is a division of application Ser. No. 08/178,176 filed Jan. 6, 1994 still pending; which is a continuation-in-part of application Ser. No. 07/929,638, filed Aug. 12, 1992, now abandoned; a continuation-in-part of application Ser. No. 08/012,370, filed Feb. 2, 1993, now U.S. Pat. No. 5,370,675; a continuation-in-part of application Ser. No. 062,364, filed May 13, 1993, now U.S. Pat. No. 5,435,805; a continuation-in-part of application Ser. No. 061,072, filed May 14, 1993, now U.S. Pat. No. 5,385,544; and a continuation-in-part of application Ser. No. 061,647, filed May 13, 1993, now U.S. Pat. No. 5,421,819.

FIELD OF THE INVENTION

This invention is directed to unique apparatus and methods for penetrating body tissues for medical purposes such as tissue ablation and fluid substance delivery, for example. The device penetrates tissue to the precise target selected in order to deliver energy to the tissue and/or deliver substances. It limits this treatment to the precise preselected site, thereby minimizing trauma to normal surrounding tissue and achieving a greater medical benefit. This device is a catheter-like device for positioning a treatment assembly in the area or organ selected for medical treatment with one or more stylets in the catheter, mounted for extension from a stylet port in the side of the catheter through surrounding tissue to the tissue targeted for medical intervention.

In particular, this invention is directed to a medical probe device with enhanced RF, resistance heating, and microwave ablation capabilities.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of targeted tissues in the body or the proximity of the target tissue to easily damaged, critical body organs, nerves, or other components.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling. The association of BPH with aging has been shown by the incidence of BPH in 50 percent of men over 50 years of age and increases in incidence to over 75 percent in men over 80 years of age. Symptoms of urinary obstruction occur most frequently between the ages of 65 and 70 when approximately 65 percent of men in this age group have prostatic enlargement.

Currently there is no nonsurgical method for treating BPH which has proven to be effective. In addition, the surgical procedures available are not totally satisfactory. Currently, patients suffering from the obstructive symptoms of this disease are provided with few options: continue to cope with the symptoms (i.e., conservative management), submit to drug therapy at early stages, or submit to surgical intervention. More than 430,000 patients per year in the United States undergo surgery for removal of prostatic tissue. These represent less than five percent of men exhibiting clinical significant symptoms.

Those suffering from BPH are often elderly men, many with additional health problems which increase the risk of surgical procedures. Surgical procedures for the removal of prostatic tissue are associated with a number of hazards including anesthesia related morbidity, hemorrhage, coagulopathies, pulmonary emboli and electrolyte imbalances. These procedures performed currently can also lead to cardiac complications, bladder perforation, incontinence, infection, urethral or bladder neck stricture, retention of prostatic chips, retrograde ejaculation, and infertility. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, dilation of the kidney pelves, chronic infection, dilation of ureters, etc.), which is not without significant consequences. Also, a significant number of patients with symptoms sufficiently severe to warrant surgical intervention are therefore poor operative risks and are poor candidates for prostatectomy. In addition, younger men suffering from BPH who do not desire to risk complications such as infertility are often forced to avoid surgical intervention. Thus the need, importance and value of improved surgical and non-surgical methods for treating BPH are unquestionable.

High-frequency currents are used in electrocautery procedures for cutting human tissue, especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture, and the tissue is separated.

Ablation of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using an electromagnetic energy which is rapidly dissipated and reduced to a non-destructive level by conduction and convection forces of circulating fluids and other natural body processes.

Microwave, radio frequency (RF), acoustical (ultrasound) and light energy (laser) devices, and tissue destructive substances have been used to destroy malignant, benign and other types of cells and tissues from a wide variety of anatomic sites and organs. Tissues treated include isolated carcinoma masses in organs such as the prostate, and glandular and stromal nodules characteristic of benign prostate hyperplasia. These devices typically include a catheter or cannula which is used to carry a radio frequency electrode or microwave antenna through a duct to the zone of treatment and apply energy diffusely through the duct wall into the surrounding tissue in all directions. Severe trauma is often sustained by the duct wall during this cellular ablation process, and some devices combine cooling systems with microwave antennas to reduce trauma to the ductal wall. For treating the prostate with these devices, for example, heat energy is delivered through the walls of the urethra into the surrounding prostate cells in an effort to ablate the tissue causing the constriction of the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

One prior art patent to Rosen et al, U.S. Pat. No. 5,150,717, issued Sep. 29, 1992, discloses a microwave aided catheter which includes a coaxial transmission line with center and outer conductors and a dielectric sheath between them. The entire contents of this patent is incorporated herein by reference.

OBJECTS AND SUMMARY OF THE INVENTION

It is one object of this invention to provide a device for penetrating tissue, through intervening tissues to the precise target tissue selected for a medical action such as tissue ablation and optional substance delivery, limiting this activity to the precise preselected site, thereby minimizing the trauma and achieving a greater medical benefit.

It is another object of this invention to provide medical probe devices with augmented RF with optional resistance heating electrodes and methods for their application for selective ablation applications.

It is a still further object of this invention to provide medical probe devices with augmented, tunable microwave antennas for selective ablation methods.

It is still another object of this invention to provide medical probe devices with resistance heating, separately or together with microwave or RF ablation capabilities, or further, RF between the stylets.

In summary, this invention relates to a medical probe apparatus for delivering ablative power to targeted tissue comprising a catheter having a stylet guide housing with at least one stylet port in a side thereof and stylet guide means for directing a flexible stylet outward through at least one stylet port and through intervening tissue to target tissue. The stylet is positioned in at least one of said stylet guide means where the stylet comprises an electrical central conductor which is enclosed within a dielectric sleeve. A conductive layer surrounds the dielectric sleeve to form a coaxial styler device, with the coaxial stylet device terminated by an antenna being capable of emitting electromagnetic field energy so as deliver the ablative power to the targeted tissues.

The electromagnetic field energy is preferably microwave energy, with the dielectric sleeve with its surrounding conductive layer being mounted for longitudinal movement on the electrical conductor to expose a selected portion of the electrical central conductor surface in the target tissue.

One embodiment provides for the conductor being enclosed within a first dielectric sleeve, such that the conductive layer surrounds the first dielectric sleeve to form a coaxial stylet device with a second dielectric sleeve surrounding said conductive layer. The coaxial stylet device terminated by an antenna is capable of emitting electromagnetic field energy to deliver the ablative power to the target tissues.

Alternatively, the medical probe device could provide for the conductive layer, the resistive element, and the electrical center conductor to be in electrical series with said target tissue and the outside grounding electrode so as to establish a radio frequency current in the target tissue.

In another embodiment, the medical probe apparatus includes a stylet positioned in a stylet guide, the stylet comprising an electrical central conductor with the conductor being enclosed within a dielectric sleeve, there being a conductive layer partially surrounding the dielectric sleeve. This styler device is capable of emitting microwave field energy to the target tissue.

Another embodiment provides for a medical probe device wherein a stylet comprises an electrical central conductor, said conductor being enclosed within an insulating sleeve, and a resistive element surrounding the conductor forward of the insulating sleeve and at the distal end of said stylet. A conductive layer surrounds the insulating sleeve, said resistive element and the distal end of said central electrode, with the resistive element coupling the central conductor and the conductive layer generating joulian heat upon the application of electromagnetic signal power thereto, thereby delivering the ablative energy to said target tissue. The resistive element comprises a radio frequency resistive paste and the electromagnetic signal power is radio frequency energy, wherein the conductive layer comprises silver metal.

BRIEF DESCRIPTION OF THE DRAWINGS

FIG. 6 is an exploded view of the RF ablation catheter shown in FIG. 1;

FIG. 7 is an isometric view of the adjuster block and tension tube assembly of the RF ablation catheter shown in FIG. 6;

FIG. 8 is a detailed view "A" of the tension tube connections shown in FIG. 7;

FIG. 11 is a side cross-sectional view of a microwave antenna stylet assembly;

FIG. 12 is a side cross-sectional view of an alternate embodiment of a microwave antenna stylet assembly;

FIG. 13 is a proximal end view of another embodiment of a microwave antenna styler assembly;

FIG. 14 is a side cross-sectional view of the microwave antenna stylet assembly embodiment of FIG. 13;

FIG. 15 is an isometric view of the microwave antenna styler assembly embodiment of FIG. 13 and FIG. 14;

DETAILED DESCRIPTION OF THE INVENTION

Figure 1:
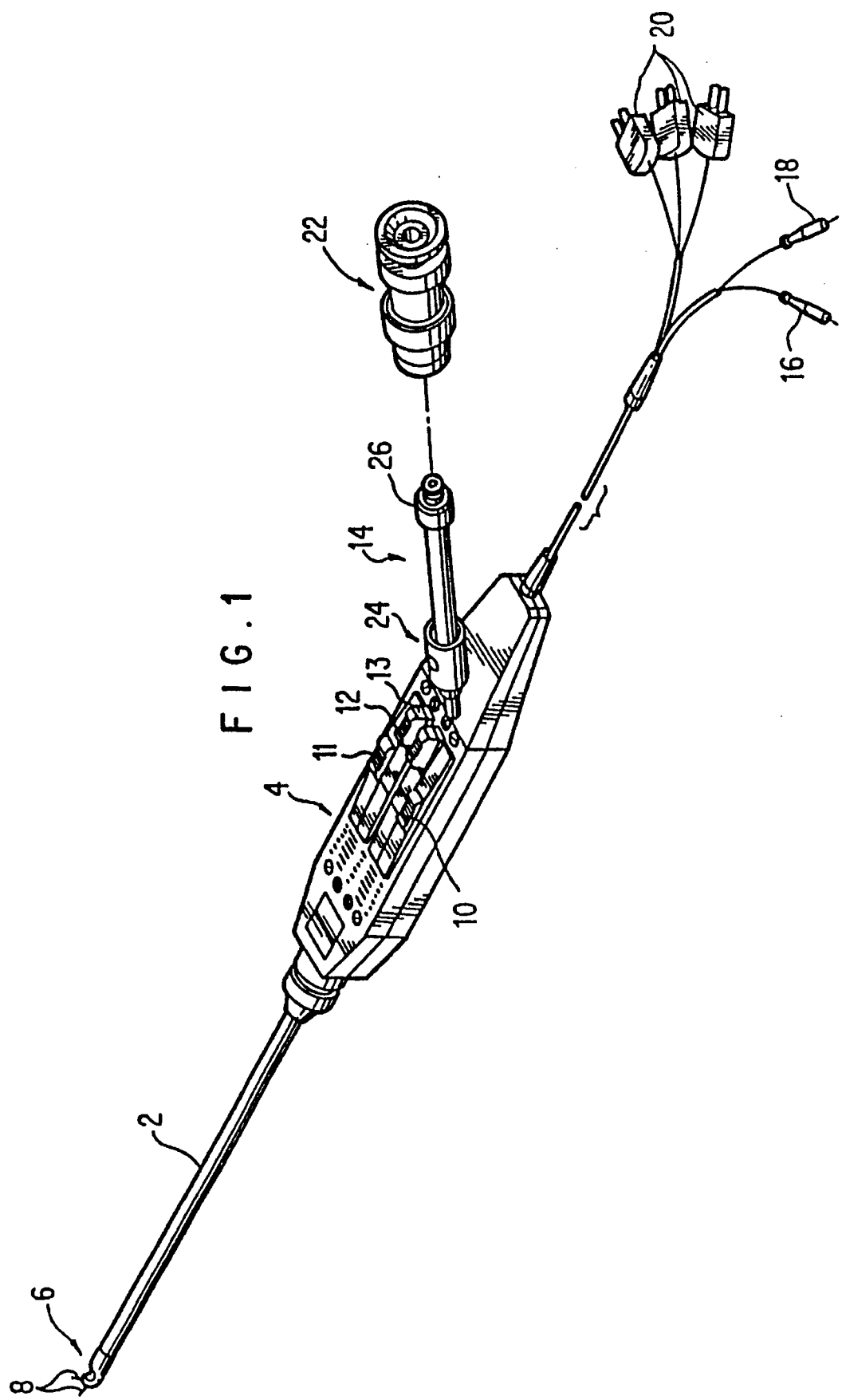
FIG. 1 is an isometric view of an RF ablation catheter embodiment with a fiber optic viewing accessory.

The device of this invention provides a precise controlled positioning of a treatment stylet in a tissue targeted for treatment, ablation or sampling from a catheter positioned in the vicinity of targeted tissues.

The term "stylet" as used hereinafter is defined to include both solid and hollow probes which are adapted to be passed from a catheter port through normal tissue to targeted tissues. The stylet is shaped to facilitate easy passage through tissue. It can be a solid wire, thin rod, or other solid shape or it can be a thin hollow tube or other shape having a longitudinal lumen for introducing fluids to or removing materials from a site. The stylet can also be a thin hollow tube or other hollow shape, the hollow lumen thereof containing a reinforcing or functional rod or tube such as a laser fiber optic filament. The stylet preferably has a sharpened end to reduce resistance and trauma when it is pushed through tissue to a target site. As will be hereafter described, the stylet can also include enhanced RF, resistance heating, and microwave apparatus, as well.

The stylet can be designed to provide a variety of medically desired treatments of a selected tissue. As a resistance heater, radio frequency electrode, or microwave antenna, it can be used to ablate or destroy targeted tissues. As a hollow tube, it can be used to deliver a treatment fluid such as a liquid to targeted tissues. The liquid can be a simple solution or a suspension of solids, for example, colloidal particles, in a liquid. Since the stylet is very thin, it can be directed from the catheter through intervening normal tissue with a minimum of trauma to the normal tissue.

The method and apparatus of this invention provide a more precise, controlled medical treatment which is suitable for destroying cells of medically targeted tissues throughout the body, both within and external to body organs. The device and method are particularly useful for treating benign prostate hyperplasia (BPH), and the device and its use are hereinafter described with respect to BPH, for purposes of simplifying the description thereof, it will be readily apparent to a person skilled in the art that the apparatus and method can be used to destroy body tissues in any body cavities or tissue locations that are accessible by percutaneous or endoscopic catheters, and is not limited to the prostate. Application of the device and method in all of these organs and tissues are intended to be included within the scope of this invention.

BPH is a condition which arises from the benign replication and growth of cells in the prostate, forming glandular and stromal nodules which expand the prostate and constrict the opening of the prostatic urethra. Glandular nodules are primarily concentrated within the transition zone, and stromal nodules within the periurethral region. Traditional treatments of this condition have included surgical removal of the entire prostate gland, digital removal of the adenoma, as well as transurethral resection of the urethral canal and prostate to remove tissue and widen the passageway. One significant and serious complication associated with these procedures is iatrogenic sterility. More recently, laser treatment has been employed to remove tissue, limiting bleeding and loss of body fluids. Balloons have also been expanded within the urethra to enlarge its diameter, with and without heat, but have been found to have significant limitations.

Microwave therapy has been utilized with some success by positioning a microwave antenna within the prostatic urethra and generating heat in the tissue surrounding the urethra with a microwave field. Coolants are sometimes applied within the catheter shaft to reduce the temperature of the urethral wall. This necessitates complicated mechanisms to provide both cooling of the immediately adjacent tissues while generating heat in the more distant prostatic tissue. This technique is similar to microwave hyperthermia. Similarly, radio frequency tissue ablation with electrodes positioned within the urethra exposes the urethral wall to destructive temperatures. To avoid this, temperature settings required to protect the urethra must be so low that the treatment time required to produce any useful effect is unduly extended, e.g. up to three hours of energy application.

One embodiment of the device of this invention previously disclosed in a parent application uses the urethra to access the prostate and positions RF electrode stylets directly into the tissues or nodules to be destroyed. The portion of the stylet conductor extending from the urethra to targeted tissues is enclosed within a longitudinally adjustable sleeve shield which prevents exposure of the tissue adjacent to the sleeve to the RF current. The sleeve movement is also used to control the amount of energy per unit surface area which is delivered by controlling the amount of electrode exposed. Thus the ablation is confined to the tissues targeted for ablation, namely those causing the mechanical constriction. Other aspects of the invention will become apparent from the drawings and accompanying descriptions of the device and method of this invention. It will be readily apparent to a person skilled in the art that this procedure can be used in many areas of the body for percutaneous approaches and approaches through body orifices.

FIG. 1 is an isometric view of an RF ablation catheter embodiment of this invention with a fiber optic viewing accessory. The flexible catheter 2, attached to handle 4, has a terminal stylet guide 6 with two stylets 8. The handle has styler sleeve tabs 10 and 11 and electrode tabs 12 and 13 as will be described in greater detail hereinafter. The handle 4 is also connected to a optical viewing assembly 14 and RF power connector 16, transponder connector 18 and thermocouple connectors 20. The portions of the catheter 2 leading from the handle 4 to the stylet guide tip 6 can optionally have a graduated stiffness. For example, the catheter can be designed to be more stiff near the handle and more flexible near the tip, or any other stiffness profiles. The catheter can be constructed of an inner slotted stainless steel tube with outer flexible sleeve such as is described in copending application Ser. No. 790,648 filed Aug. 11, 1991 (corresponding to published Australian patent application Serial No. 9210858), the entire contents of which are incorporated herein by reference. It can also be made of coiled or braided wire to which an outer sleeve is bonded.

The fiber optic viewing assembly in this embodiment includes a lens focusing assembly 22, a lens viewing assembly support connector 24 assembly attached to a male quick disconnect connector 26 by flexible tubing 28.

Figure 2:
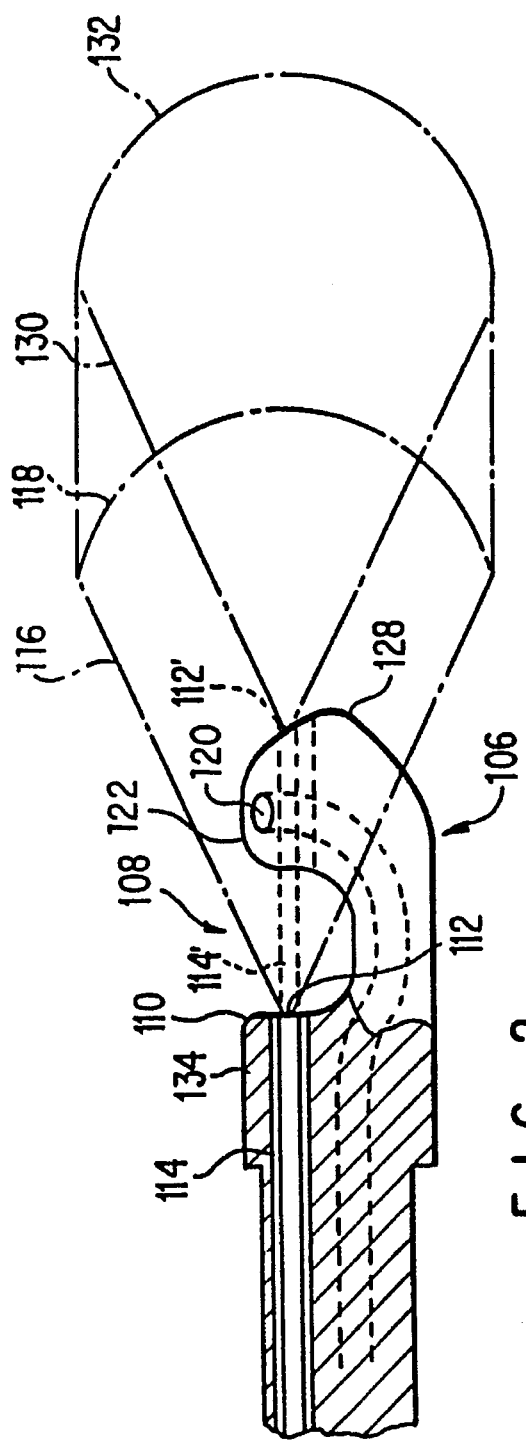
FIG. 2 is a fragmented cross-sectional view of a preferred catheter tip and stylet guide housing of this invention.

FIG. 2 is a fragmented cross-sectional view of a preferred catheter tip and stylet guide housing of this invention. The solid catheter tip 106 has a lateral depression or saddle 108 therein having a central axis approximately perpendicular to a plane through the central axis of the tip. The depression 108 has a proximal wall 110. The depression 108 can extend up to approximately half of the thickness of the housing, but at least sufficiently to unblock the viewing surface of the viewing tip 112 of the fiber optic 114. The fiber optic viewing tip 112, when positioned at the opening in wall 11 0, provides a field of view with lateral margins 116 and a terminal margin 118. This includes the path of stylets extended outward through ports 120.

Figure 3:
FIG. 3 is a distal end view of the catheter tip and style guide housing shown in FIG. 2.

FIG. 3 is a distal end view of the catheter tip and styler guide housing shown in FIG. 2. The proximal end of depression 108 is split to form two projections or ears 122 and 124 which define a longitudinal or axial or longitudinal groove or saddle 126 extending from the depression 108 to the terminal tip 128 of the catheter 106. Groove 126 opens the field of view for the viewing tip 112 when in the solid line position shown in FIG. 2 and permits extension of the fiber optic and its tip through the longitudinal groove to the dotted line positions 114' and 112'. In the latter position, the field of vision has side margins 130 and a terminal margin 132. This permits the operator to examine the inner duct surfaces ahead of the catheter tip. In an alternative embodiment, the groove 126 can be replaced with a hole in the end of the tip having a size and position to permit extension of the fiber optic 114 therethrough.

The fiber optic 114 is positioned in a passageway 134 which is sufficiently larger than the fiber optic to permit flow of flushing liquid around the fiber optic to the exit in wall 110. The flushing liquid flow clears debris from the viewing tip. The inner walls of the duct (not shown) surrounding the catheter tip 106 during use confine the liquid flow, so the liquid continues to pass over the fiber optic tip even when it has been advanced to the dotted line position. Return flushing liquid lumina 136 and 138 extend through wall 110 for constant removal of contaminated flushing liquid.

Figure 4:
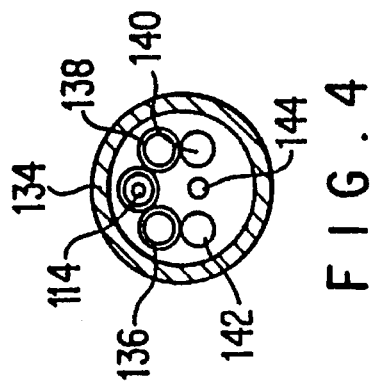
FIG. 4 is a proximal end view of the unassembled catheter tip and stylet guide housing shown in FIG. 2, showing the lumina for the components thereof.

FIG. 4 is a proximal end view of the unassembled catheter tip and stylet guide housing shown in FIG. 2, showing the lumina for the components thereof. The stylets are advanced and retracted through stylet lumina 140 and 142 to the stylet ports 120. The fiber optic is advanced and retracted through fiber optic lumen 134. The contaminated flushing fluid is removed through flushing fluid return lumina 136 and 138. Temperature sensor lumen 144 is used to house leads of a temperature sensor (not shown).

Figure 5:
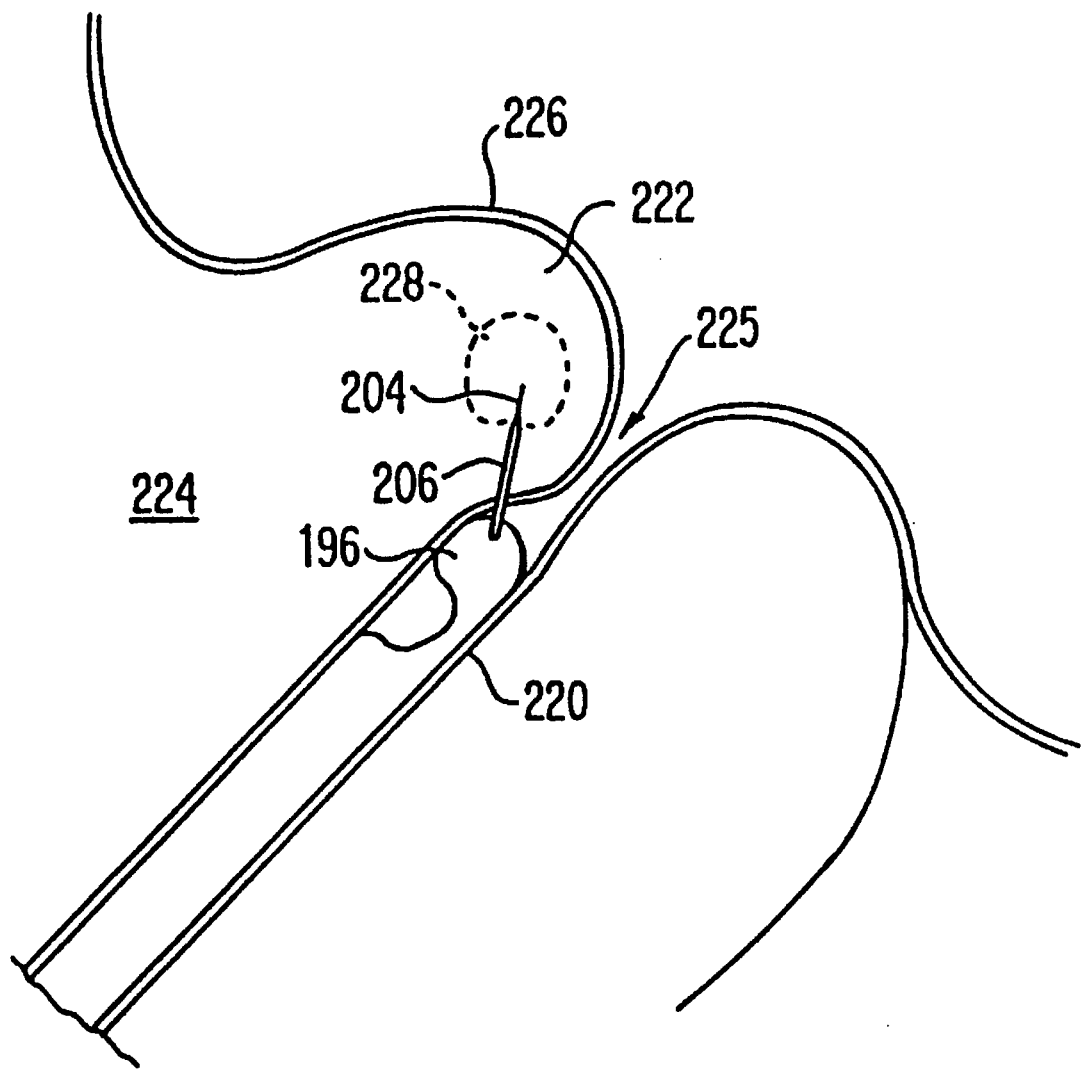
FIG. 5 is a schematic view of a stylet deployment into a portion of a prostate protruding into the urinary bladder.

FIG. 5 is a schematic view of a single stylet of FIG. 1 or 2 shown deployed to treat a portion of a prostate protruding into the urinary bladder. The solid catheter tip 196 is positioned at the end of the urethra 220. Cell proliferation in the upper end 222 of the prostate 224 has caused it to protrude into space normally occupied by the urinary bladder, pushing a portion of the bladder wall 226 into the cavity and forming a restriction 225 beyond the end of the urethra. The stylet sleeve 206 and electrode 204 are extended at an angle of about 30° through the urethral wall into a portion of the protruded prostate, and RF current is applied to form the lesion 228. This will reduce the protruded prostate, promoting its retraction from the urethral wall and opening the restriction of the outlet end of the urethra. The catheter having a desired angle can be selected from those having predetermined angles to precisely orient the styler and effect precise penetration of prostate tissue which extends beyond the end of the urethra, for example.

FIG. 6 is an exploded view of the RF ablation catheter assembly shown in FIG. 1. The upper handle plate 276 has two central slots 278 and 280 through which the electrode control slides 10 are attached to respective left electrode slide block 282 and right electrode slide block 284. Sleeve control slides 12 and 13 are attached through outer slots 286 and 288 to respective left sleeve slide block 290 and right sleeve slide block 292. Fiber optic receptor housing 30 is mounted on the proximal surface of the upper handle plate 276. The electrical receptor 294 is received in respective cavities 296 and 298 in the respective upper handle plate 276 and lower handle plate 300 attached thereto. The lower handle plate 300 has a central cavity 302 which accommodates the electrode and sleeve slide blocks and associated elements.

Microswitch activator blocks 304 (only left sleeve block shown) are connected to the sleeve slide blocks 290 and 292. They are positioned to actuate the microswitches 306 when the respective sleeve block (and sleeve attached thereto) have been advanced. The microswitches 306 hold the respective RF power circuits open until the respective sleeves are advanced to a position beyond the urethra wall and into the prostate to prevent direct exposure of the urethra to the energized RF electrodes. Extension of the sleeve 5 mm beyond the guide is usually sufficient to protect the urethra.

The tension-torque tube assembly 308 is mounted in the distal end of the housing in the receptor 310.

FIG. 7 is an isometric view of the adjuster block and tension tube assembly 308 of the RF ablation catheter shown in FIG. 6. The torque tube 312 extends from the torque coupler 314 through the twist control knob 316 to the stylet guide 6. Bending flexure of the torque tube 312 during use lengthens the path from the handle to the guide tip 6. To prevent a resulting retraction of the stylet sleeve and electrode components when the torque tube 312 is flexed, a tension tube 318 having a fixed length and diameter smaller than the inner diameter of the torque tube 312 is provided. The distal end of the tension tube 318 is securely attached to the stylet guide 6, and the proximal end 320 is secured to the adjuster block 322, for example by an adhesive. The axial or longitudinal position of the adjuster block 322 can be adjusted to insure the stylets are initially positioned just inside the outlet ports in the stylet guide 6. Torque coupler 314 is mounted on the coupler block 324. Twist control knob stop pin 326 extends into a groove (not shown) and limits rotation of the control knob 316.

FIG. 8 is a detailed view "A" of the distal end tension tube connections of the tension tube shown in FIG. 7. The tension tube 318 is securely connected to the proximal end 328 of the stylet guide 6, for example by a length of shrink tubing 330.

Figure 9:
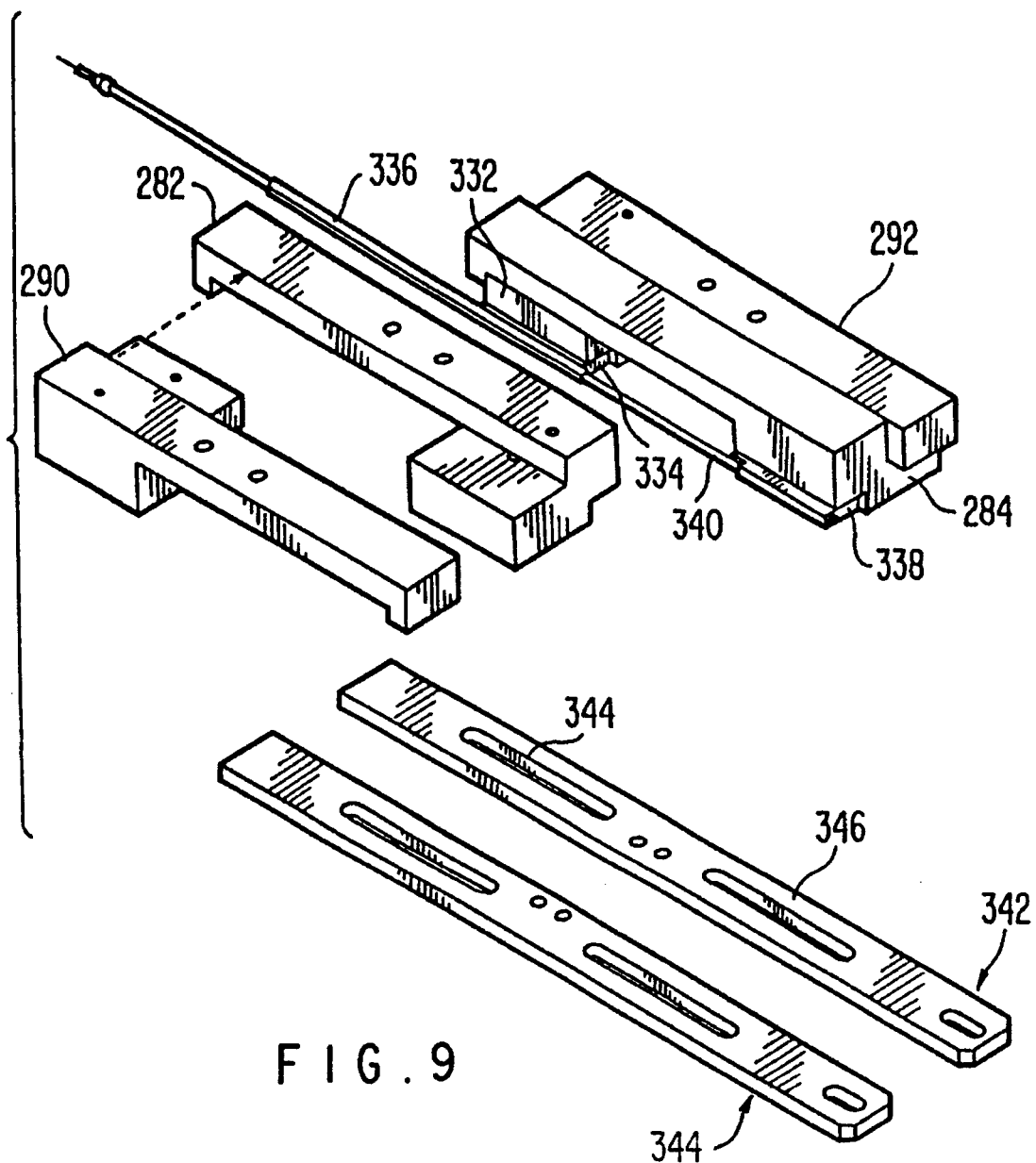
FIG. 9 is an exploded view of the sleeve and electrode slide block assembly of the embodiment shown in FIG. 6.

FIG. 9 is an exploded view of the sleeve and electrode slide block assembly of the embodiment shown in FIG. 6. The right sleeve slide block 292 has a projection 332 which extends inward under the right electrode slide block 284. Right sleeve connector 334 is mounted to the inner end of the projection 332, secured to the end of the proximal end of the sleeve 336. Right electrode connector 338 is attached to an inner surface of the electrode slide block 284 and is secured to the proximal end of electrode 340. The right sleeve and electrode slide blocks 292 and 284 are slidingly attached to the right friction adjustment rail 342 by screws (not shown) through slots 344 and 346, the screws being adjustable to provide sufficient friction between the blocks and the rail 342 to provide secure control over the stylet movement. The left sleeve slide block 290 and left electrode slide block 282 are mirror replicas of the right blocks and are similarly mounted on the left friction rail 344. The left sleeve and electrodes are not shown.

Figure 10:
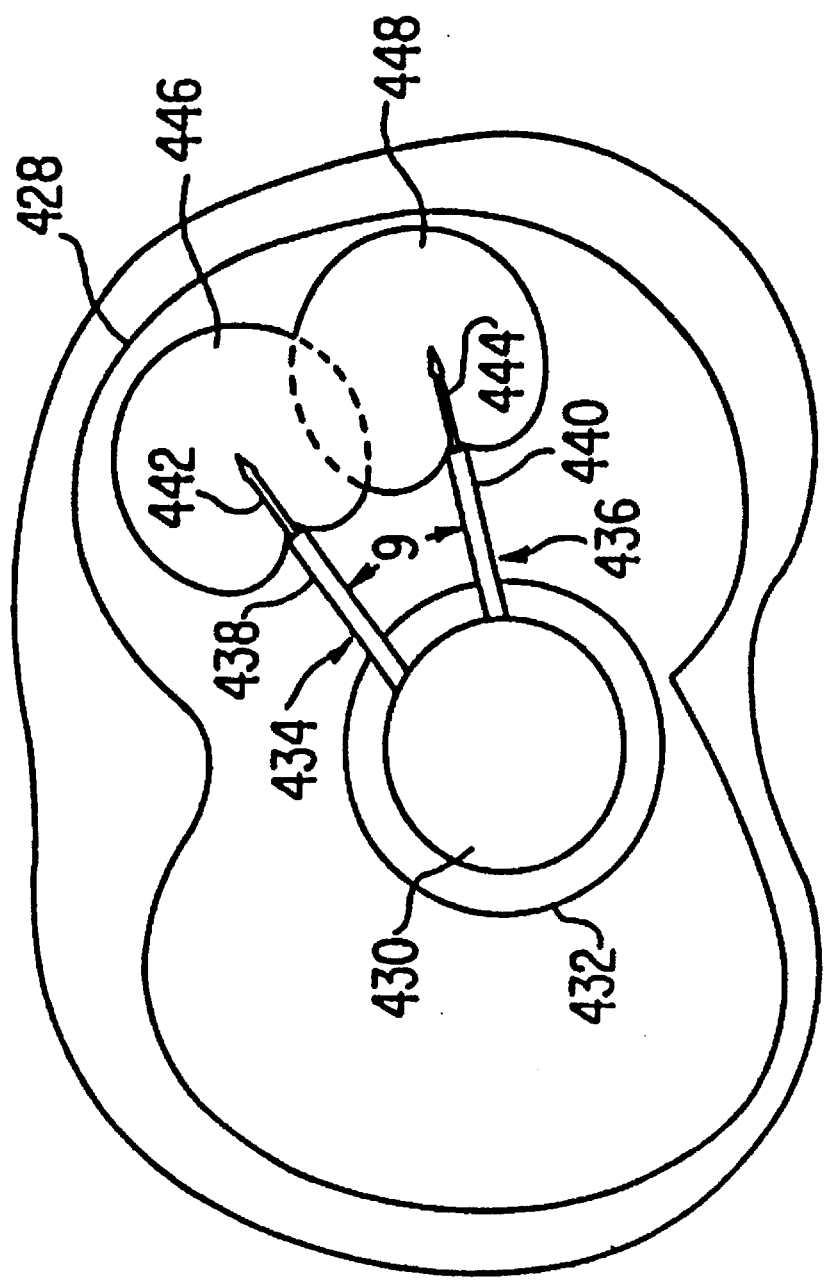
FIG. 10 is a schematic view of a deployment of two stylets in a prostate showing a stylet orientation for overlapping ablation zone method.

FIG. 10 is a schematic view of a deployment of two stylets in a prostate showing stylet orientation for overlapping ablation zone method of this invention. For purposes of illustration but not by way of limitation, the prostate has been selected for this explanation, and application of this method and assembly to other areas of the body are intended to be included.

The tissues to be treated for the treatment of BPH are located in the transition zone 428 of the prostate. A catheter of this invention 430 has been inserted up the urethra 432 to a position adjacent the prostate. Two stylets 434 and 436 have been passed through the urethra wall 432 through forward movement of tabs 10 and 12 (FIG. 1) and through surrounding tissue into targeted tissues. The non-conducting sleeves 438 and 440 have been retracted by rearward movement of sleeve tabs 10 to expose a portion of the respective electrical conductors 442 and 444 at the end of each stylet. The angle between the axes of the stylets in this embodiment, "g", is less than 180°, preferably less than 110° For most overlapping ablations, angles of 15° to 90°, and more usually from 20° to 70° are most practical. A grounding plate (not shown) is placed on the body exterior.

When electrodes 442 and 444 are supplied with RF current, the circuit from the electrodes to a grounding plate is closed. The current density flowing through the tissue passes through targeted tissues to be treated, creating lesions having the approximate cross-sectional shape of overlapping zones 446 and 448. The current density rapidly decreases as a function of distance, limiting the size of the lesions. In this manner, lesions can be caused to overlap to form a larger lesion, increasing the efficiency of the treatment. It will be readily apparent that these processes can be carried out concurrently, as described, or sequentially, and these variations are intended to be included in this invention.

FIG. 11 is a side view of a stylet assembly 800 which comprises a center electrode 805, an insulating or dielectric sleeve 803 completely surrounding the electrode 805, and another conductor layer 801 surrounding the insulator 803. This layer could be a conductive coating, metal braid, sleeve, or other type of layer including a sheath. Dielectric sleeve 807 supports the stylet electrode 805 and insulator 803 in the catheter as described hereinbefore for FIGS. 1 to 10. In FIG. 11, the sleeve 807 is of insulating material. The metallic or conductive layer 801 as an outer conductor, with electrode 805 as the inner conductor, layer 801 and electrode 805 separated by insulator 803 comprise the coaxial line delivering microwave energy to the antenna, which is the extension portion of electrode 805.

U.S. Pat. No. 5,150,717 to Rosen et al, issued Sep. 29, 1992, cited above, discloses a microwave aided balloon angioplasty device with a guide filament. This patent suggests that a typical catheter utilizes a central conducting electrode 805 with a dielectric sleeve 803 made of polyvinyl chloride (PVC), and the outer conductive layer may be a conductor or a conducting sheath in typical coaxial cable configuration.

The microwave frequency signals are applied to central electrode 805 and the conductor layer 801 after the electrode has been extended into the intended tissue as described above in conjunction with FIGS. 1 to 10. The further the distance that the electrode 805 is extended into the tissue, the larger the area that can be affected by the applied signal. Field 811 can be seen in FIG. 11 to be radiating away from electrode 805 and conductor layer 801 and operating as a microwave antenna. By adjusting the length of electrode 805 extending out from dielectric 803 and the conductor layer 801, the operator is able (1) to control the output microwave frequency, for example, from 915 MHz to 2.45 GHz; (2) to vary the volume of tissue to be ablated; and (3) to fine-tune the antenna to the load (here a prostate gland). The desired effect is to raise the temperature of the affected tissue to 45° C. or more to cause internal lesions which will eventually be absorbed by the body and reduce the prostatic pressure on the urethra. Because the length of the extension of the electrode 805 beyond the edge of the dielectric 803 and conductor 801 is adjustable by the operator, the amount of microwave field energy emitted into the surrounding tissue can be carefully modulated and monitored.

FIG. 12 is a side view of a stylet assembly 700 which comprises a center electrode 705, an insulating or dielectric sleeve 703 completely surrounding the electrode 705, and another conductor layer 707 surrounding the insulator 703. The conductor layer 707 is the sleeve of the stylet that supports the conductor as it is deployed. This layer could be a conductive coating, metal braid, sleeve, or other type of layer including a sheath, but generally would be an elongated cylindrical tube of flexible metal. The metallic or conductive layer 707 as the outer conductor, with electrode 705 as the inner conductor, and separated by insulating sleeve 703 comprise the coaxial line delivering microwave energy to the antenna, which is the extension portion of electrode 705.

The stylet assembly 700 operates in a similar manner to the styler assembly in FIG. 11. The stylet assembly, including the center electrode 705, insulating layer 703, and conductive sleeve 707, is carried inside a catheter as explained above in earlier figures when inserted into a body canal, such as a urethra. When the catheter is in place adjacent to the prostate tissue to be ablated, the stylet assembly 700 is deployed out from the catheter and passes through the urethra. Further deployment of the stylet places the tip 705 of the stylet assembly 700 in the immediate vicinity of the prostate tissues to be ablated. The electrode 705 is then further deployed into the selected tissue and energized with the requisite amount of microwave energy. As described earlier, the resultant energy emitted from the distal end of stylet assembly 700 into surrounding tissue heats the tissue above about 45° C. which reduces the mass of the selected tissue. By adjusting the length that the electrode 705 extends out beyond conducting layer 707, the operating physician can alter the frequency of the emitted signal, adjust the amount of tissue to be destroyed, and compensate for the changing load as the tissue is ablated.

FIG. 13 is an end view of a stylet assembly of an embodiment which is a combination of FIGS. 11 and FIG. 12. FIG. 11 includes the center electrode 805 surrounded by a conductive layer 801 and separated by insulating layer 803, the sleeve 807 being a dielectric, or non-conducting sleeve. FIG. 12 includes the center conductor 705 surrounded by the dielectric layer 703, where the outer conductor is the sleeve 707 itself. In FIGS. 13, 14 and 15, sharpened stylus tip 901 is shown extended out beyond the dielectric layer 903. In this embodiment, however, the layer 903 has had deposited on it, or braided around it, or by some other manner, a metallized (i.e., conductive) layer 905. Metal guide 907 is the sleeve, which in this embodiment is conductive, i.e., metallic, while in other embodiments described above it is insulating, or comprised of a dielectric or non-conductive material. In this embodiment, both the center conductor 901 and the dielectric layer 903 with associated conductive layer 905 are deployed into target tissue. That is, after the stylet 901 is advanced via use of its sharpened tip into target tissue, the dielectric sleeve 903 with accompanying conductive layer 905 can be advanced so as to fine tune the applied microwave frequency, applied power level, or load upon the system as a whole. Conductive sleeve 907 in this embodiment can also act as the return electrode for microwave transmission line purposes if the stylet electrode 901 is advanced into target tissue only far enough so that none of the dielectric layer 903 exposes its joint conductive layer.

Figure 16:
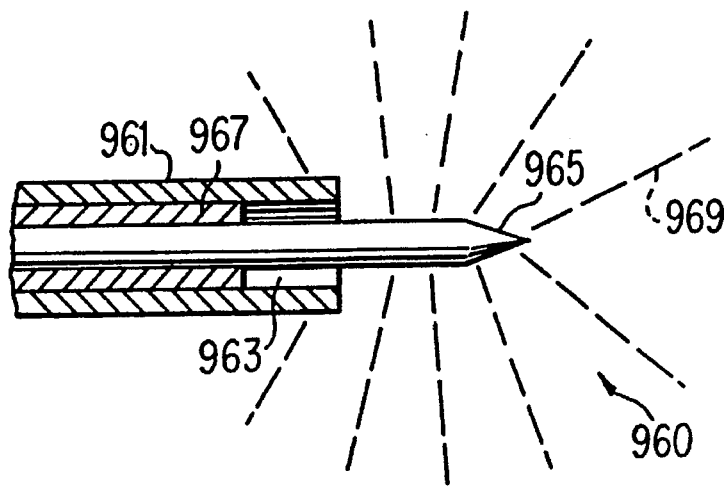
FIG. 16 is a cross-sectional view of a radio frequency, resistive heating embodiment.

FIG. 16 illustrates still another embodiment of the present invention. Central electrode 965 is controllable in and out from the stylet assembly 960 by the operator. Surrounding the center electrode 965, except for the leading edge thereof at the distal end, is insulating or dielectric layer 967. Replacing the last part of the insulating layer 967 is a resistive layer 963. This layer 963 can comprise a resistive layer, paste, or film, the resistive value of which being controlled by the thickness of the layer, or the composition of the layer, such as, comprising a predetermined percentage of metallic particles, carbon, or boron, for example. Surrounding the insulating area 967 and the resistive layer 963 at the forward edge of insulating layer 967 is conductor layer 961.

This embodiment utilizes the effects of radio frequency signals. The applied signal is applied between central electrode 965 and conductive layer 961 after deployment of electrode 965 into target tissue. The RF current would flow via the center electrode 905 and conductive layer 961 partially through the resistive layer 963. This causes localized heating of the desired tissue to be ablated. However, if there is no return connection to conductive layer 961 in the stylet assembly 960, but a return is provided by an external body grounding plate, then there are two heating effects. One effect being the localized heating effect of the resistive layer 963, and the other effect being that of the RF current flowing through the targeted tissue. Typical values include four watts of applied power with about 60° C. being the temperature of the electrode 965.

It is possible, of course, to apply microwave frequency power to the device shown and described in conjunction with FIG. 16 to effect local resistive heating and microwave field ablation.

With regards to FIGS. 11, 12, and 13, the central electrode can be deployed by the operator as far as the electrode tabs 12 and 13 allow (see FIG. 1). The extra electrical lead for the conducting sheath could be provided for in the same channels as provided for the RF power connector 16, transponder, connector 18, or thermocouple connectors 20.

Figure 17:
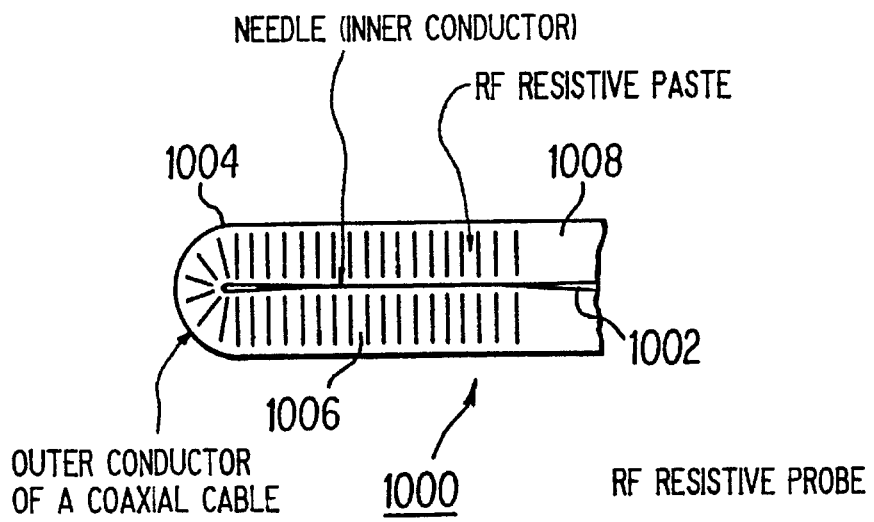
FIG. 17 is a cross sectional view of an alternate embodiment of a radio frequency, resistive heating embodiment.
Figure 18:
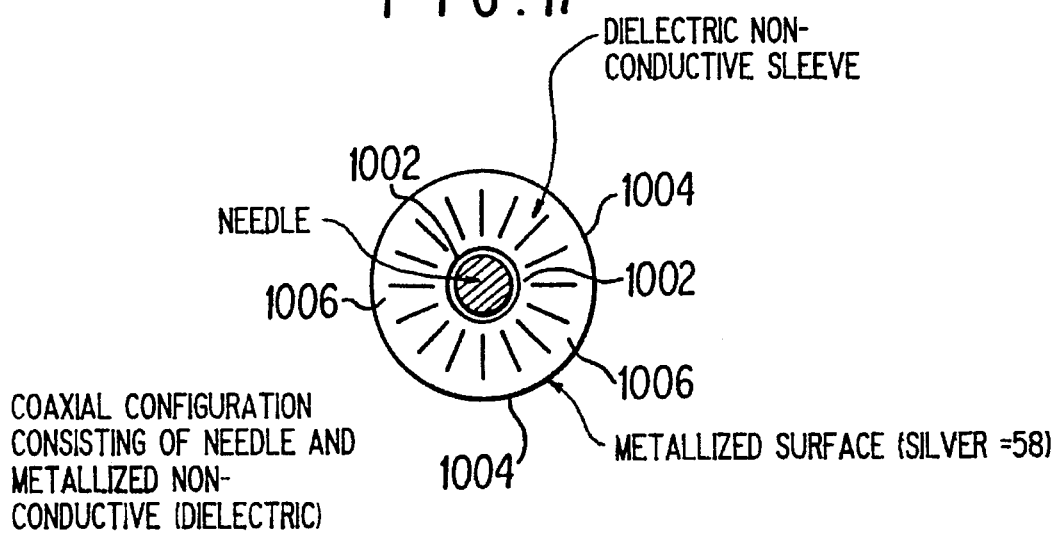
FIG. 18 is a proximal end view of the RF, resistive heating embodiment of FIG. 17.

An alternative to the embodiment of FIG. 16 is discussed in conjunction with FIGS. 17 and 18. FIG. 17 is a side view of stylet assembly 1000. Sleeves to accompany the stylet are not shown in this figure but would be similar to conductive or non-conductive sleeves shown and described in earlier figures. Stylet assembly 1000 is constructed to form a coaxial cable. That is, there is an inner conductor 1002 surrounded radially, and directly in front of, at its distal end, an outer conductor, separated at the end of the assembly 1000 by an RF resistance material 1006. This material could be the same RF layer, paste, or film 903 as seen above in FIG. 16. That is, at RF or other applied frequencies, the current flowing between the inner conductor 1002 and the outer conductor 1004 would heat up the RF resistive layer 1006. By adjusting the frequency and power of the applied signal, the amount of heat radiated by the stylet assembly 1000 can be modulated or adjusted. Immediately behind the RF resistive material 1006 is insulating or dielectric material 1008 to space the inner and outer conductors apart to prevent shorts from occurring by an accidental touching of the outer conductor by or with the center conductor electrode.

The stylet assembly 1000 in FIG. 17 is shown rounded at the distal end thereof, but it could be made sharper if this conductor is going to pierce through tissue to target tissue.

FIG. 18 is a view of the cable shown in FIG. 17 from the proximal end thereof. Inner conducting needle 1002 is surrounded by the dielectric non-conductive material or sleeve 1006. The metallized outer conductor 1004 is comprised of the metal silver or other appropriate conductor, while the dielectric sleeve 1006 could comprise well known plastics, ceramics, etc. The RF resistance material 1006 could comprise a paste which includes carbon particles, etc., for example.

Although preferred embodiments of the subject invention have been described in some detail, it will be understood by those skilled in the art, that obvious variations can be made herein without departing from the spirit and scope of the invention as defined by the appended claims.

We claim:

1. A medical probe system for delivering ablative power to target tissue, comprising a catheter having a stylet port, a stylet assembly disposed within the catheter and having a central electrode with a sharp distal tip for puncturing tissue and an outer conductor disposed coaxially about the central electrode, means for advancing the styler assembly outwardly through the stylet port and through intervening tissue with a length of the central electrode extending beyond the outer conductors and into the target tissue, means for applying microwave power to the central electrode so that the central electrode functions as an antenna for radiating microwave energy into the target tissue, and means for adjusting the length of the central electrode extending beyond the outer conductor to thereby adjust the frequency of the microwave power delivered to the target tissue.

2. The medical probe system of claim 1 further including a non-conductive sleeve mounted between the central electrode and the outer conductor for longitudinal movement relative to the central electrode to expose a selected portion of the central electrode in the target tissue.

3. The medical probe system of claim 1 further including an electrically grounded element which cooperates with the stylet in delivering microwave power to the target tissue.

4. A medical probe system for delivering ablative power to target tissue, comprising a catheter having at least two stylet ports, at least two stylet assemblies disposed within the catheter and having central electrodes with sharp distal tips for puncturing tissue and outer conductors disposed coaxially about the central electrodes, means for advancing the stylet assemblies outwardly through the stylet ports and through intervening tissue with lengths of the central electrodes extending beyond the outer conductors and into the target tissue, means for applying microwave power to the central electrodes so that the central electrodes function as antennas for radiating microwave energy into the target tissue, and means for adjusting the lengths of the central electrodes extending beyond the outer conductors to thereby adjust the frequency of the microwave power delivered to the target tissue.

5. The medical probe system of claim 4 further including non-conductive sleeves mounted between the central electrodes and the outer conductors for longitudinal movement relative to the central electrodes to expose selected portions of the central electrodes in the target tissue.

6. The medical probe system of claim 4 further including an electrically grounded element which cooperates with at least one of the stylets in delivering microwave power to the target tissue.

\* \* \* \* \*